United States Patent [19]
Frank

[11] 3,950,799
[45] Apr. 20, 1976

[54] RESPIRATORY DISTRESS STIMULATOR SYSTEM

[75] Inventor: Ulrich Anton Frank, Yardley, Pa.

[73] Assignee: Hoffmann-La Roche Inc., Nutley, N.J.

[22] Filed: Dec. 13, 1975

[21] Appl. No.: 424,385

Related U.S. Application Data

[62] Division of Ser. No. 239,264, March 29, 1972, abandoned.

[52] U.S. Cl. .................................. 5/369; 5/349; 128/DIG. 29
[51] Int. Cl.² ................................... A47C 27/08
[58] Field of Search ........................... 5/348, 349; 128/DIG. 29, 2 S

[56] References Cited
UNITED STATES PATENTS

| | | | |
|---|---|---|---|
| 647,374 | 4/1900 | Brendel | 5/348 R |
| 1,285,391 | 11/1918 | Robertson | 5/348 R |
| 1,772,310 | 8/1930 | Hart | 5/348 R |
| 3,148,391 | 9/1964 | Whitney | 5/348 R |
| 3,605,138 | 9/1971 | Tucker | 5/348 R |
| 3,631,438 | 12/1971 | Lewin | 128/DIG. 29 |
| 3,727,606 | 4/1973 | Sielaff | 128/DIG. 29 |
| 3,792,873 | 2/1974 | Buchner | 5/348 R |
| 3,798,686 | 3/1974 | Gaiser | 5/348 R |

Primary Examiner—Kenneth Downey
Attorney, Agent, or Firm—Samuel L. Welt; George M. Gould; Mark L. Hopkins

[57] ABSTRACT

A patient care system for monitoring respiratory distress problems and providing therapeutic treatment comprising, a sensor for generating patient derived respiratory activity signals, detecting an apnea episode from the signals, and providing in response to a detected apnea episode, stimulation of the patient by a momentary inflation of a pneumatic means adapted for placement under the patient to raise the patient and induce loss of equilibrium for startling the patient into a natural respiration pattern.

5 Claims, 4 Drawing Figures

RESPIRATORY DISTRESS STIMULATOR SYSTEM

This is a division of application Ser. No. 239,264, filed Mar. 29, 1972.

BACKGROUND OF THE INVENTION

The present invention relates to an apnea monitoring and therapeutic system and more specifically a system directed at stimulation of a patient in respiratory distress.

The cessation of respiration or the inability to get one's breath often referred to as apnea, is a serious problem which becomes dangerous especially in premature infants where such occurrences are frequent. It is understood that repeated attacks as well as prolonged attacks of apnea are factors which carry a poor prognosis both for life and for subsequent mental development resulting from irreversible cerebral damage sustained during these apneic episodes. The best prospect of reducing harmful effects of late-occurring apnea is through constant surveillance preferably using some automated device to alert attendants so that stimulation through resuscitation can begin promptly. As a consequence, apnea monitoring of premature infants has become an accepted practice in most institutions.

Management of apnea monitoring in the newborn, particularly in prematures, for the most part includes sensitive devices for detecting apnea events. Upon detection of an apnea episode a visual or audible alarm is generated, to call the attending nurse for prompt manual stimulation of the infant in an attempt to terminate the episode by restoring normal breathing. Alertness and responsiveness of the nursing staff is important as it becomes more difficult to obtain a positive response to stimulation the longer the apnea persists. Naturally then, most apnea monitors are designed to provide an early alarm. Unfortunately, however, most of these apnea episodes are of a short duration and occur almost randomly during any day of neonatal life. Thus, they place an unnecessary burden on the nurse to the extent that in some cases it is conceivable that the alarms may even be neglected.

The purpose of the present invention is to avoid some of the problems incurred in apnea monitoring by closing the loop of the automated monitoring system, to provide a therapeutic action by early stimulation of the respiratory distressed patient. The preferred innovative technique of automatic mechanical stimulation in the present embodiment is directed to suddenly induce a loss of equilibrium and a falling sensation to, in effect, startle the infant into a natural respiration pattern. This is conveniently accomplished by sudden inflation, through regulating the pneumatic pressure, of a small pneumatic mattress which is preferably placed under the upper half of the infant's body.

PREFERRED EMBODIMENT OF THE INVENTION

Figure 1:
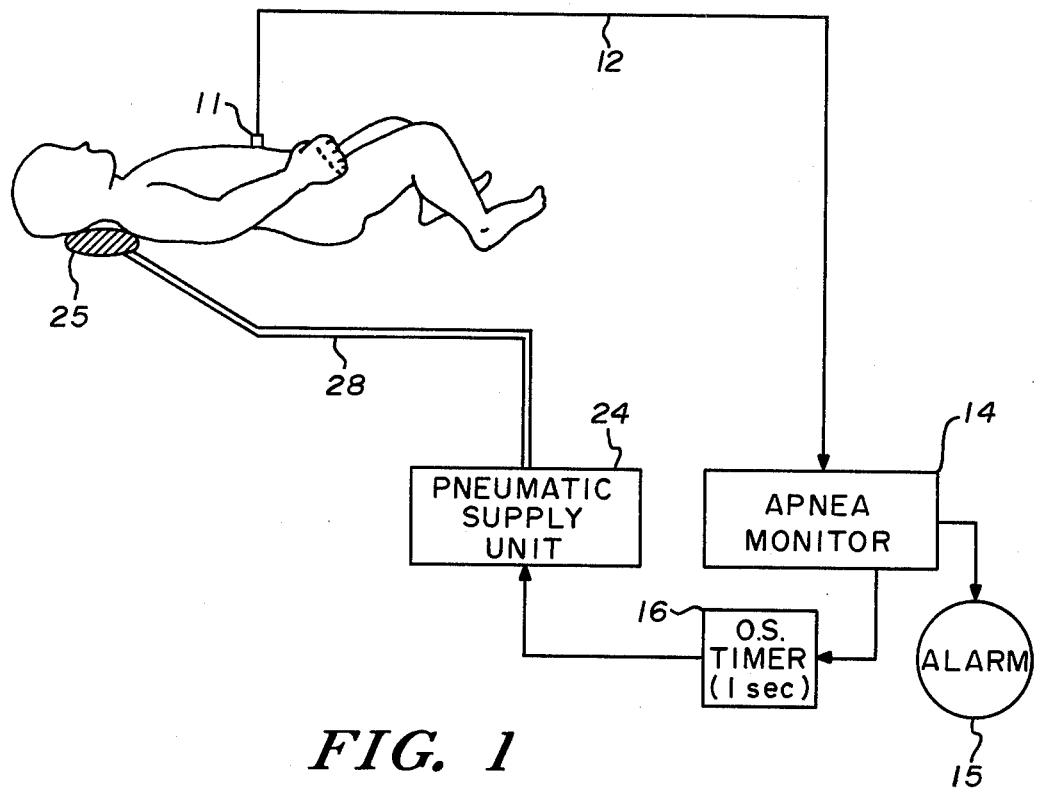
FIG. 1 is a schematic diagram in block form of the invention.

With reference to the drawings there is shown in FIG. 1 a preferred embodiment of the invention comprising a sensor 11 secured by suitable means to a patient, the respiratory activity detected by sensor 11 being converted to an electrical signal which is conducted by lead 12 to an apnea monitor 14. Respiratory distress problems are detected from the respiratory signals by an apnea monitor 14 to emit signals indicative of apnea episodes for energizing an alarm 15 and for activating a one shot unit 16 serving as a one second timer in the present embodiment.

Figure 2:
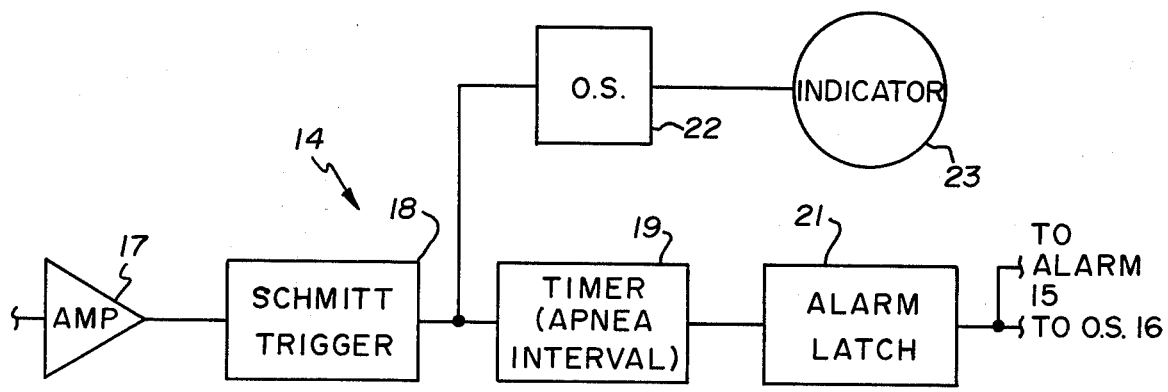
FIG. 2 is a schematic diagram in block form of a typical apnea monitor 14 illustrated in FIG. 1.

The apnea monitor 14 could take the configuration of a number of conventional apnea monitors now commercially available irrespective of whether the basis of their operation is based on the impedance pneumography, capacitance respirometry, or any other technique for detecting the apnea episode. A typical one of such apnea monitors is shown in FIG. 2 including, an input amplifier 17 which is driving a Schmitt trigger 18 adapted to be responsive during the period its input signal penetrates above a predetermined threshold level for which the Schmitt trigger is set. The Schmitt trigger output is connected to a timer 19 having a timing capacitance which will react in response to a predetermined interval for denoting an apnea interval to in turn produce an output for exciting an alarm latch 21, the output of which is connected to the one shot unit 16, illustrated in FIG. 1. The Schmitt trigger 18 output is also used for energizing a one shot unit 22 which in turn drives an indicator 23 representative of the respiration activity of the patient.

With reference back to FIG. 1, the duration of the one shot timer 16 will determine the period during which stimulation is to be applied to the patient. The one shot timer 16 is connected for driving a pneumatic supply unit which in turn is pneumatically coupled through suitable tubing to an inflatable pneumatic stimulator 25 placed under the patient. In a patient having an apnea episode, the pneumatic stimulator is momentarily inflated to induce a sudden loss of equilibrium which, in effect, startles the patient back into a normal respiration pattern.

Figure 3:
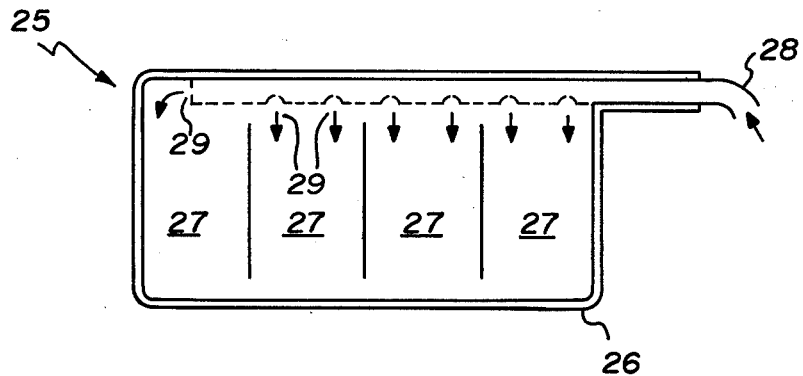
FIG. 3 is a top plan view of one embodiment of a pneumatic stimulator 25 shown in FIG. 1.

An embodiment of the pneumatic stimulator is illustrated in FIG. 3, wherein there is a rectangular shaped flexible casing constructed of, for example, an elastomeric material which might be rubber, neoprene, polyethelene etc. The pneumatic stimulator has an air mattress configuration provided by four partially separated areas 27 each of which is supplied with air through a relatively rigid tube 28 via apertures 29. The rigid tube is advantageous in that because of its rigid nature the air mattress cannot be folded or bent-over at an area where one depends on the passage of air through the several segments for proper air flow. Otherwise, as is experienced with conventional air mattresses, when folded over the continuity of air flow is obstructed between adjacent segments to prevent the air mattress from being completely inflated. By use of the tubular mattress construction, the height of the mattress when fully inflated can be better regulated over the entire area of the mattress, and thus prevent the pneumatic stimulator from billowing up when inflated to otherwise possibly cause the patient to be moved to one side. A normal size of the air mattress for an infant might be about 5 inches by 8 inches to allow for considerable movement of the neonate without having the head and neck slide off when used under the head and neck.

Figure 4:
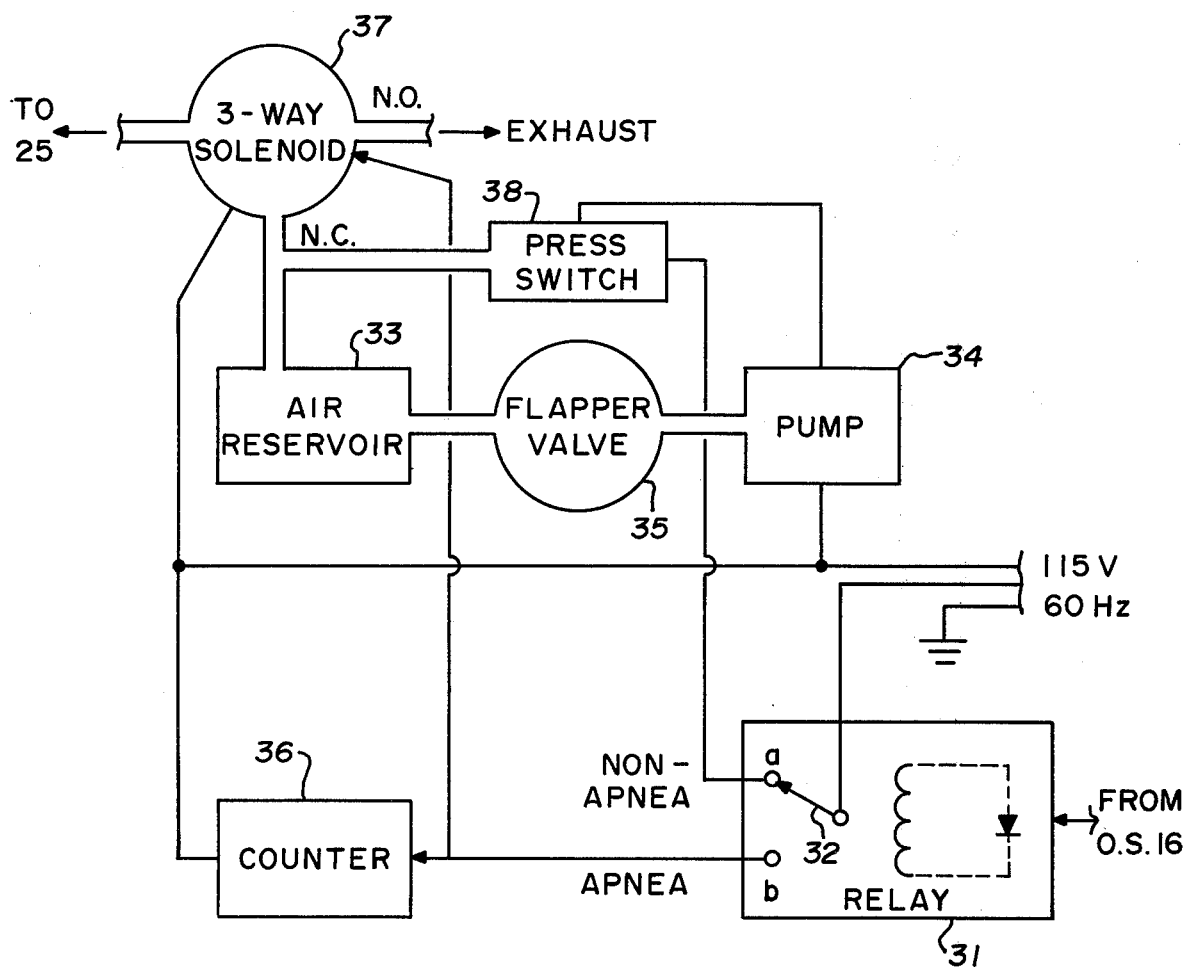
FIG. 4 is a schematic diagram in block form of a preferred embodiment of the pneumatic supply unit 24 depicted in FIG. 1.

An embodiment of the pneumatic supply unit 24, is shown in FIG. 4, wherein the input signal from one shot 16 is connected to a relay unit 31 which controls a relay arm 32 to be either connected to a first terminal (*a*) denoted as a non-apnea terminal or a second terminal (*b*) denoted as an apnea terminal. In its normally assumed position the relay arm 32 is connected to terminal (*a*) which, in turn, is connected to a pressure switch 38, that is connected via pneumatic tubing from a gas reservoir 33, preferably air, which is electrically connected to a pump 34. Air reservoir 33 and pump 34 are also pneumatically connected via a flapper valve 35. With relay arm 31 in its normal condition (*a*) the pressure switch 38 senses the pressure in air reservoir 33 which, if below a predetermined pressure valve, will be supplied with pressurized air from pump 34 through one-way flapper valve 35.

The terminal point (*b*) of relay 31 is connected via an apnea lead to a counter 36 and to a three-way solenoid valve 37, which is pneumatically coupled from air reservoir 33 to the pneumatic stimulator 25 and through an exhaust opening. Reservoir 33 assures the availability of a large quantity of pressurized air to momentarily inflate the pneumatic stimulator, and also avoids delay during the inflation cycle of the pneumatic stimulator. In the present embodiment the time to inflate the pneumatic stimulator takes less than ½ second assuming a 15 psi reservoir pressure source and ¼ inches diameter connecting tube with a final 4 psi system pressure, including the stimulator.

In operation, since relay arm 31 is normally connected to the (*a*) terminal, pump 34 will be charging air reservoir 33 through the flapper valve 35 during periods when the pressure switch 38 senses approximately 10% below a predetermined pressure for the air reservoir. Respiratory movements which are detected by sensor 11 are fed to the apnea monitor 14. Upon detection of an apnea episode the one shot timer 16 is activated.

Relay 31 is activated from the one shot unit 16 for a period of 1 second during which time relay arm 32 enables power to be supplied to the three-way solenoid valve and an apnea episode count is made on counter 36. The three-way solenoid valve is open allowing the air from reservoir 33 to momentarily inflate pneumatic stimulator 25 to stimulate the patient by suddenly raising the patient up in the air to introduce his sudden loss of equilibrium and, in effect, startle the patient into normal respiration. At the end of the 1 second period relay arm 32 goes back to terminal (*b*) to, in effect, close off the three-way solenoid valve from air reservoir 33 to pneumatic stimulator 25 and open the exhaust opening of the three-way valve to the pneumatic stimulator 25 for deflating the pneumatic stimulator. Because air has been used from the air reservoir 33, this will be sensed by the pressure switch 38 which will activate the pump 34 to in turn provide pressurized air in the air reservoir 33 via the flapper valve 35, to, in effect, set the system up ready for the next apnea episode when it is detected.

If desired, if the stimulation is found to be unsuccessful in breaking the apnea episode a continuing alarm might be provided for until the patient is attended to or a second nurse's alarm might be initiated within a 5-second period or any other prescribed time period that would be suitable for providing such a second alarm.

I claim:

1. An inflatable pneumatic unit of the air mattress configuration for use in a respiratory stimulator system comprising:
    a unitary inflatable casing constructed of an elastomeric material and having a plurality of open-ended intercommunicating elongated segments, said segments opening via at least one end thereof into the interior of the casing proximate at least one side of the casing; and
    a singular relatively rigid apertured pneumatic tube extending into and along the interior of said at least one side of said casing and proximate the one ends of said segments, the apertures of said tube being predeterminably located to be in close communication with said segments, said tube being arranged within said casing for preventing said casing from becoming folded over and for providing uniform rapid momentary inflation and deflation thereof.

2. A unit according to claim 1 wherein a longitudinal portion of the exterior of said relatively rigid pneumatic tube constitutes a part of the exterior of said casing and said apertures are provided in that longitudinal portion of said tube in communication with the interior of said casing.

3. A unit according to claim 1 wherein the shape of said casing is substantially rectangular, and wherein said segments are arranged to extend substantially parallel to each other and substantially perpendicular to the portion of said pneumatic tube extending into the interior of said casing.

4. A unit according to claim 3 wherein said relatively rigid pneumatic tube enters the interior of said casing of one corner thereof and runs at least the length of said one side of said casing.

5. A pneumatic stimulating device comprising an inflatable elastomeric casing having in the interior a plurality of open-ended segmented areas coupled together by way of at least one internal common area, and a substantially rigid pneumatic tube extending into the interior of said casing, said pneumatic tube extending along said common area and being predeterminably apertured to provide a corresponding predetermined number of tube ports to be situate proximate the portion of each said segmented area coupling into said common area for enabling a uniform rapid inflation and deflation of said casing.

* * * * *